US012614617B2

(12) United States Patent
  Burkholz et al.

(10) Patent No.:  US 12,614,617 B2
(45) Date of Patent:       Apr. 28, 2026

(54) COLLECTING AND CONNECTING VASCULAR ACCESS DATA THROUGHOUT THE CONTINUITY OF CARE

(71) Applicant: Becton, Dickinson and Company, Franklin Lakes, NJ (US)

(72) Inventors: Jonathan Karl Burkholz, Salt Lake City, UT (US); Matthew Prince, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 14 days.

(21) Appl. No.: 18/625,664

(22) Filed: Apr. 3, 2024

(65)                Prior Publication Data
US 2024/0347151 A1      Oct. 17, 2024

Related U.S. Application Data

(60) Provisional application No. 63/459,103, filed on Apr. 13, 2023.

(51) Int. Cl.
  *G16H 10/60*        (2018.01)
  *A61M 5/168*        (2006.01)
  *G16H 15/00*        (2018.01)
(52) U.S. Cl.
  CPC ........ *G16H 10/60* (2018.01); *A61M 5/16836* (2013.01); *G16H 15/00* (2018.01); *A61M 2205/18* (2013.01); *A61M 2205/3327* (2013.01); *A61M 2205/3375* (2013.01); *A61M 2205/502* (2013.01); *A61M 2205/52* (2013.01)
(58) Field of Classification Search
  None
  See application file for complete search history.

(56)              References Cited

U.S. PATENT DOCUMENTS

| | | |
|---|---|---|
| 2006/0020490 A1 | 1/2006 | Staton |
| 2015/0209114 A1* | 7/2015 | Burkholz ................ A61M 5/14 |
| | | 600/584 |
| 2015/0356254 A1 | 12/2015 | Lee |
| 2017/0311819 A1* | 11/2017 | Lee ................... A61B 5/02007 |
| 2018/0182491 A1* | 6/2018 | Belliveau ................ A43B 3/34 |
| 2019/0358387 A1* | 11/2019 | Elbadry .............. A61B 5/1459 |
| 2023/0001105 A1 | 1/2023 | Rothenberg et al. |
| 2024/0139432 A1 | 5/2024 | Burkholz et al. |
| 2024/0139433 A1 | 5/2024 | Burkholz et al. |

OTHER PUBLICATIONS

Weiner et al. (âUltrasound-Guided Vascular Access: A Comprehensive Reviewâ Journal of Cardiothoracic and Vascular Anesthesia, vol. 27, Issue 2, 345-360) (Year: 2013).*

* cited by examiner

*Primary Examiner* — Christopher B Tokarczyk
(74) *Attorney, Agent, or Firm* — Kirton McConkie; Whitney Blair; Kevin Stinger

(57)              ABSTRACT

Systems and methods for collecting and connecting vascular access data throughout the continuity of care of a vascular access are provided. A patient's historic vascular access data can be stored and made accessible during subsequent attempts to access the patient's vasculature. Additional vascular access data can be generated and stored during the subsequent attempts to access the patient's vasculature. By collecting and connecting the vascular access data, the vascular access data can enable a clinician to be more successful throughout the continuity of care of a vascular access.

20 Claims, 15 Drawing Sheets

Continuity of Care

COLLECTING AND CONNECTING VASCULAR ACCESS DATA THROUGHOUT THE CONTINUITY OF CARE

RELATED APPLICATIONS

This application claims the benefit of U.S. Provisional Patent Application No. 63/459,103, which was filed on Apr. 13, 2023, which is incorporated herein in its entirety.

BACKGROUND

Catheters are commonly used for a variety of infusion therapies. For example, catheters may be used for infusing therapeutic agents or fluids into a patient. Catheters may also be used for withdrawing blood from the patient. There are a variety of catheters commonly used in a medical setting, including, for example, peripherally-inserted central catheters, midline catheters, central venous catheters, dialysis catheters, and arterial catheters. A common type of catheter device includes a catheter that is over-the-needle. As its name implies, the catheter that is over-the-needle may be mounted over an introducer needle having a sharp distal tip.

The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient. To verify proper placement of the introducer needle and/or the catheter in the blood vessel, a clinician generally confirms that there is "flashback" of blood in a flashback chamber of the catheter assembly. Once placement of the needle has been confirmed, the catheter may be left in place for future blood withdrawal or fluid infusion.

Although catheter indwell performance (i.e., how long the catheter can be safely left in the vasculature) has improved in recent years, there remains a significant number of complications that may develop throughout the intended dwell time of a vascular access device. These complications may include dislodgement, infiltration, extravasation, phlebitis, catheter-related infection, and loss of patency, among others.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to systems and methods for collecting and connecting vascular access data throughout the continuity of care of a vascular access. A patient's historic vascular access data can be stored and made accessible during subsequent attempts to access the patient's vasculature. Additional vascular access data can be generated and stored during the subsequent attempts to access the patient's vasculature. By collecting and connecting the vascular access data, the vascular access data can enable a clinician to be more successful throughout the continuity of care of a vascular access.

In some embodiments, a method for collecting and connecting vascular access data may include storing historic vascular access data representing a history of a patient's vascular access, presenting the historic vascular access data during an access of the patient's vasculature, collecting additional vascular access data during the access of the patient's vasculature, and storing the additional vascular access data with the historic vascular access data.

In some embodiments, the historic vascular access data may comprise one or more images of the patient's vasculature.

In some embodiments, the additional vascular access data may comprise one or more images of the patient's vasculature.

In some embodiments, presenting the historic vascular access data during the access of the patient's vasculature may comprise presenting the historic vascular access data during a site assessment before placing a vascular access device in the patient's vasculature or while performing placement support during placement of the vascular access device in the patient's vasculature.

In some embodiments, collecting the additional vascular access data during the access of the patient's vasculature may comprise collecting the additional vascular access data during the site assessment or while performing the placement support.

In some embodiments, the additional vascular access data collected during the access of the patient's vasculature may comprise placement initial state baseline documentation.

In some embodiments, collecting the additional vascular access data during the access of the patient's vasculature may comprise collecting the additional vascular access data during indwell of a vascular access device.

In some embodiments, the method may further comprise processing the additional vascular access data to generate one or more alerts, status, or reports.

In some embodiments, the one or more alerts, status, or reports may be generated during indwell of a vascular access device that is used for the access of the patient's vasculature.

In some embodiments, the additional vascular access data collected during the access of the patient's vasculature may identify a removal of a vascular access device that is used for the access of the patient's vasculature.

In some embodiments, a method for connecting and collecting vascular access data throughout continuity of care may include: storing historic vascular access data representing a history of a patient's vascular access, presenting the historic vascular access data during an access of the patient's vasculature, collecting vascular access data during a site assessment or placement support of the access of the patient's vasculature, collecting vascular access data representing a placement initial state baseline documentation for the access of the patient's vasculature; and collecting vascular access data during indwell of a vascular access device used for the access of the patient's vasculature.

In some embodiments, the method may further include collecting vascular access data representing a removal of the vascular access device.

In some embodiments, the method may further include collecting vascular access data representing an experience of the access of the patient's vasculature.

In some embodiments, the vascular access device may include a catheter and the vascular access data collected during indwell of a vascular access device used for the access of the patient's vasculature may represent one or more of: catheter movement or displacement, catheter kinking, dislodgement events, extravasation, infiltration, thrombus development, phlebitis, patency indicators, blood flow characteristics, fluid administration flow characteristics, procedural events, line draw tubing, or probe or sensor position.

In some embodiments, the method may further include processing the vascular access data to automatically detect the procedural events.

In some embodiments, a system for collecting and connecting vascular access data throughout continuity of care may include: a database storing historic vascular access data representing a history of a patient's vascular access, one or more monitoring devices that are configured to present the historic vascular access data during an access of the patient's vasculature, and one or more imaging devices configured to generate additional vascular access data during the access of the patient's vasculature and to store the additional vascular access data in the database in association with the historic vascular access data.

In some embodiments, the system may further include one or more doppler devices configured to generate further vascular access data during the access of the patient's vasculature and to store the further vascular access data in the database in association with the historic vascular access data and the additional vascular access data.

In some embodiments, the one or more imaging devices may be configured to generate the additional vascular access data during a site assessment or placement support of the access of the patient's vasculature.

In some embodiments, the one or more imaging devices may be configured to generate the additional vascular access data during indwell of a vascular access device used for the access of the patient's vasculature.

In some embodiments, the one or more monitoring devices may be configured to present the historic vascular access data during a site assessment or placement support of the access of the patient's vasculature.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

4

Figure 3B:
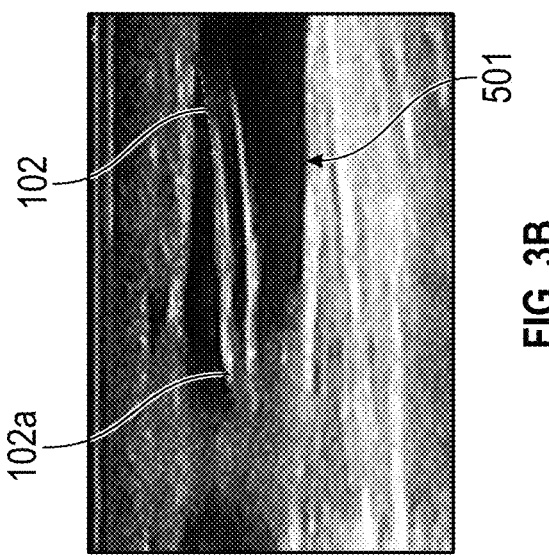
FIG. 3A is a partial cross-sectional view of a vascular access device that is configured in accordance with one or more embodiments when placed on the skin.
Figure 3A:
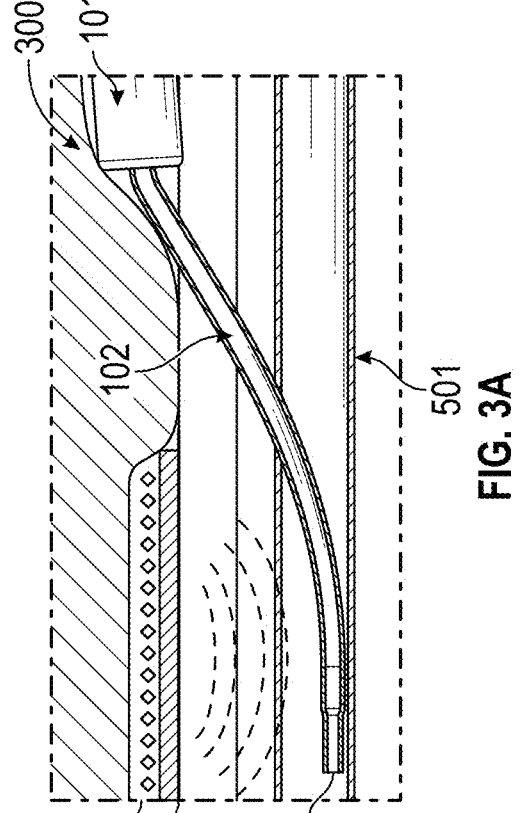
Figure 3C:
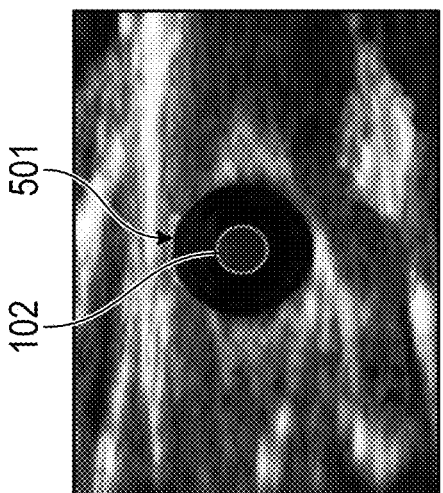
Figure 4:
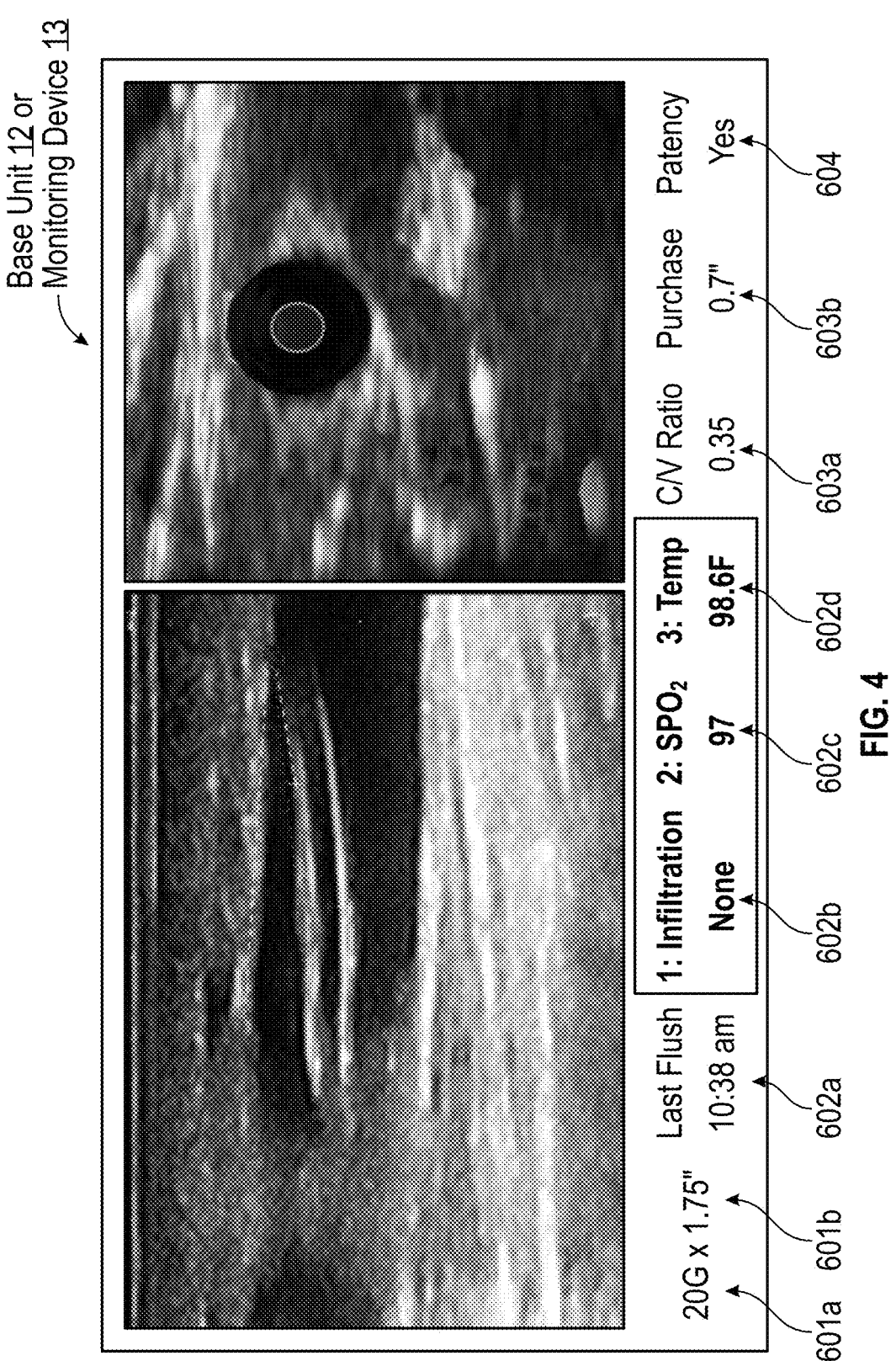
Figure 5:
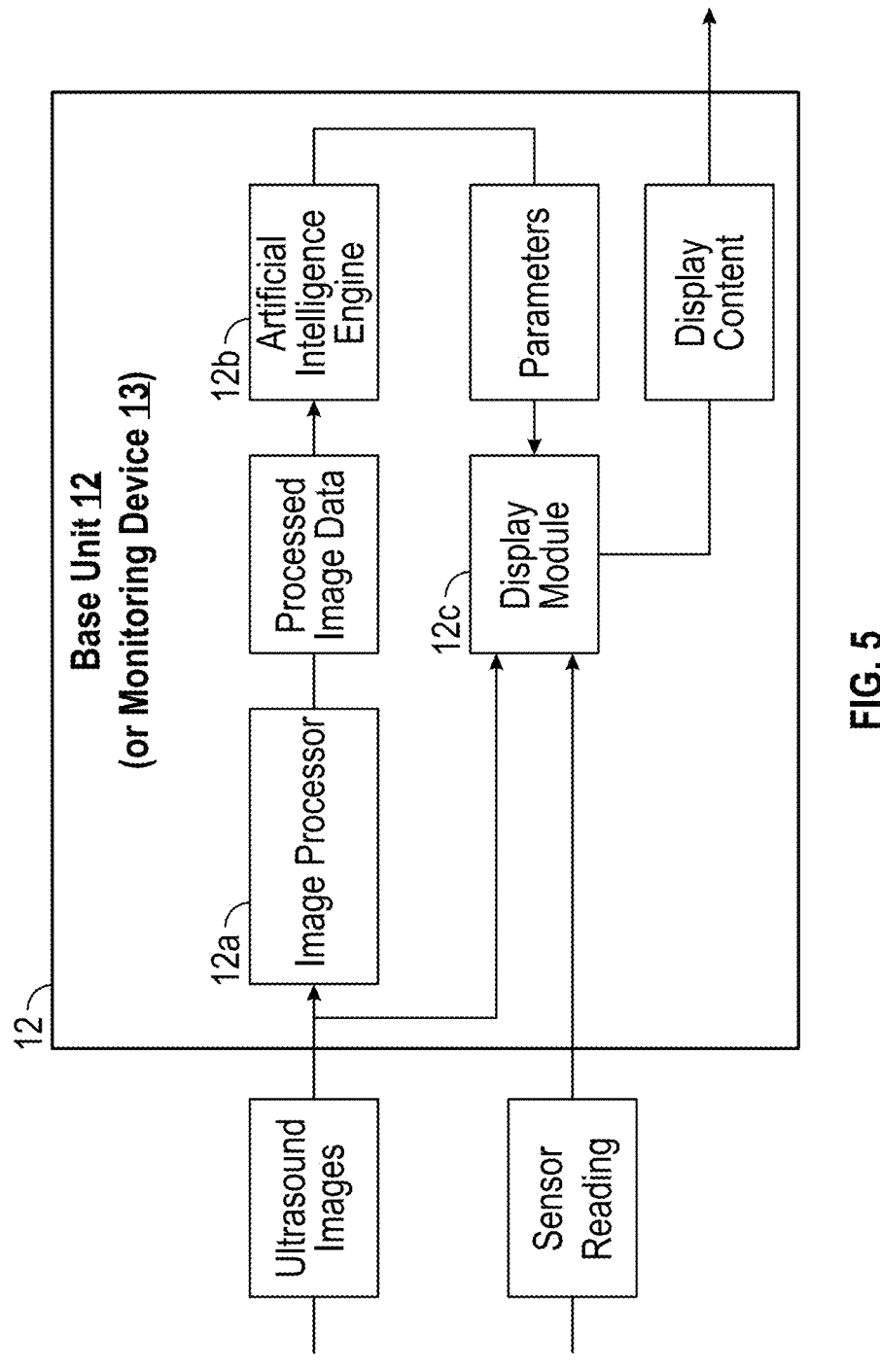
Figure 6A:
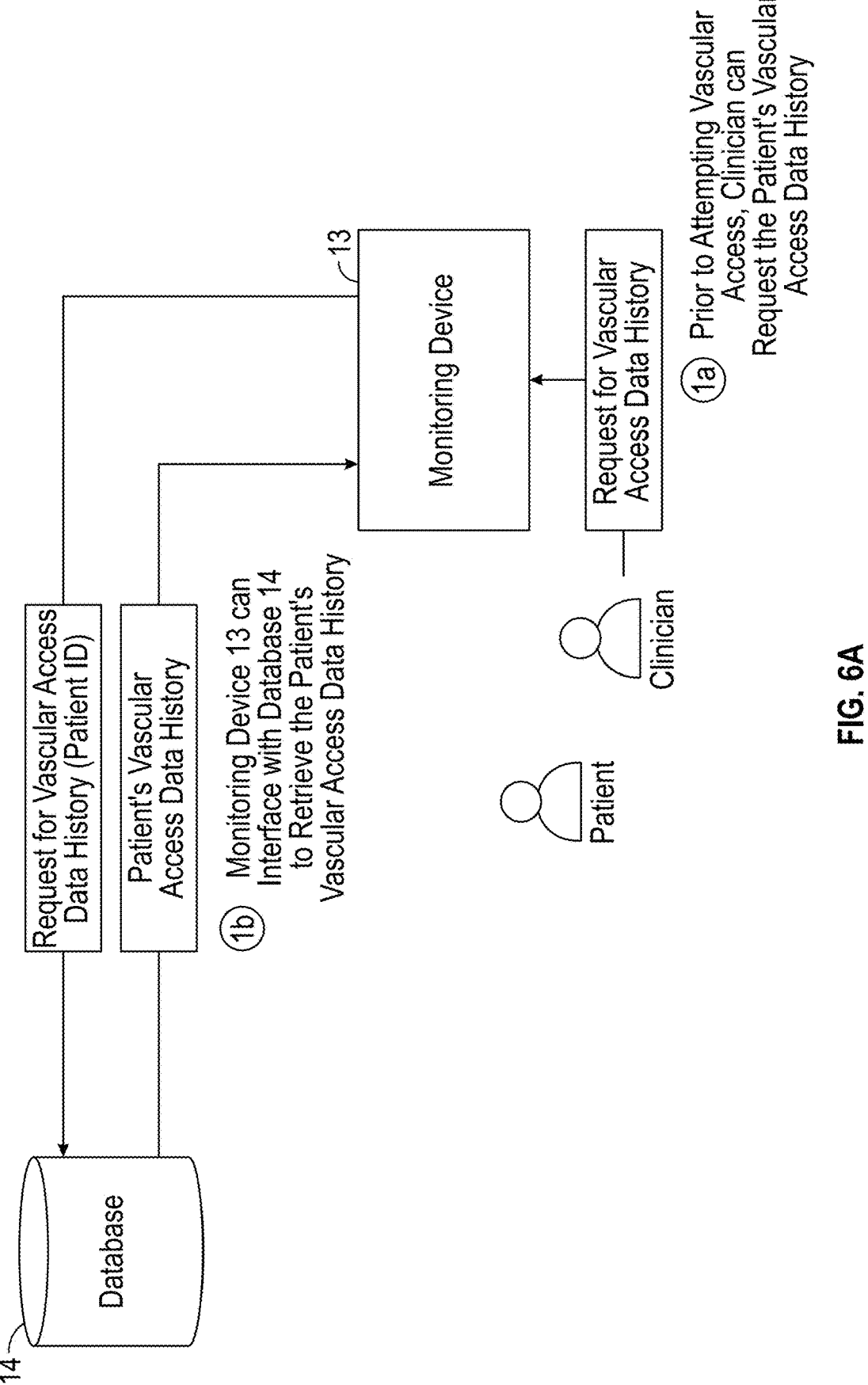
Figure 6B:
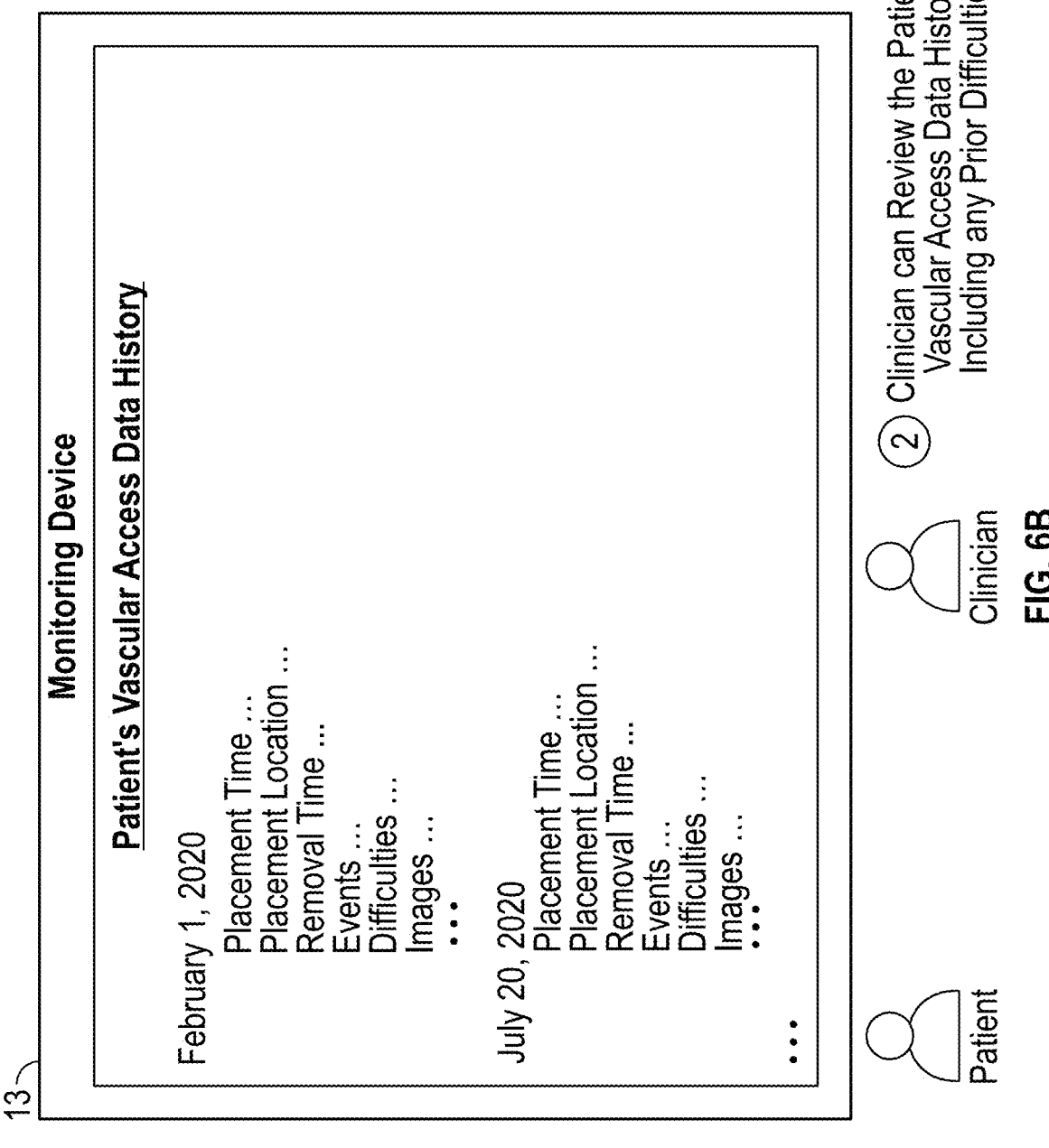
Figure 6C:
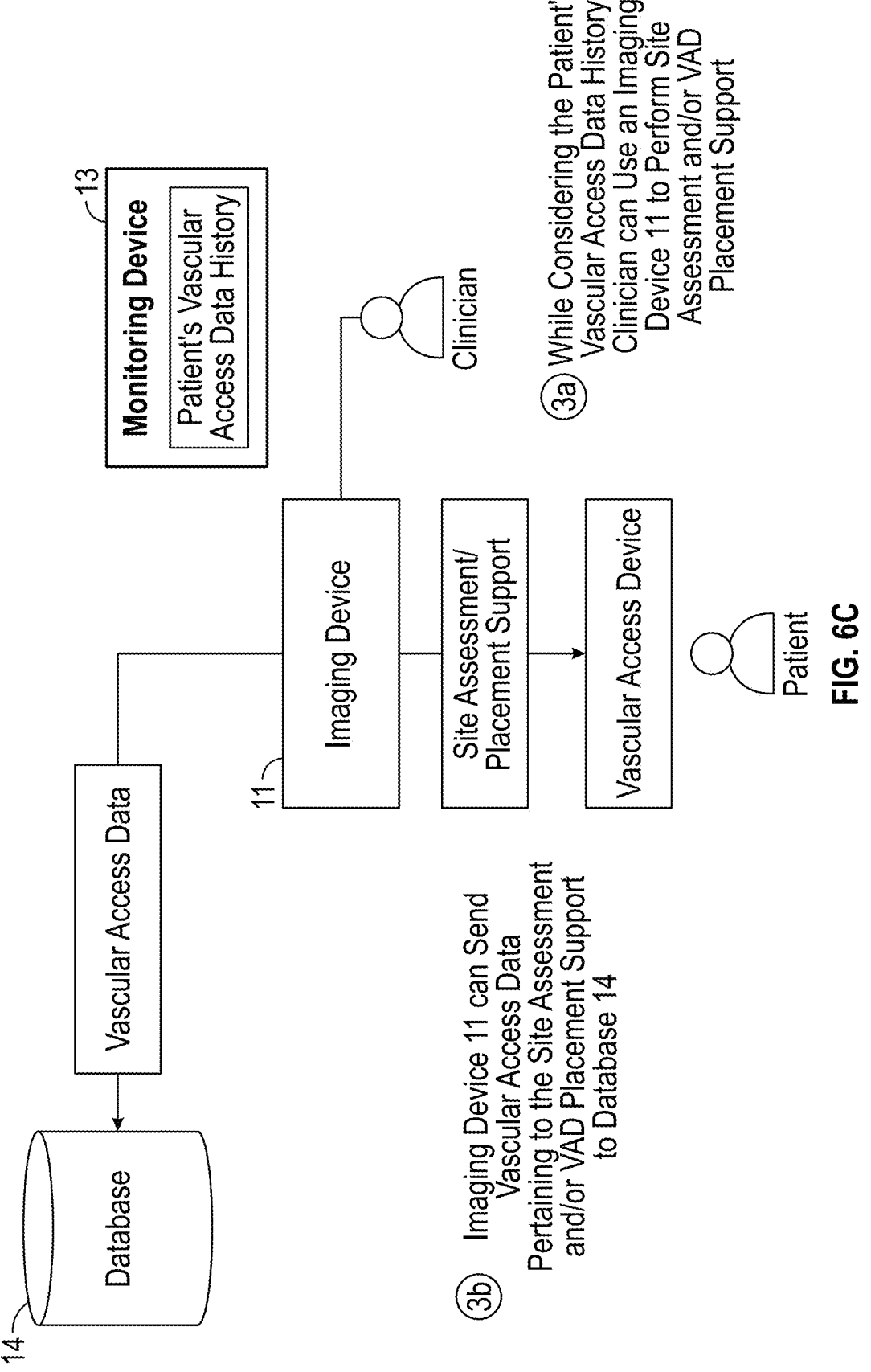
Figure 6D:
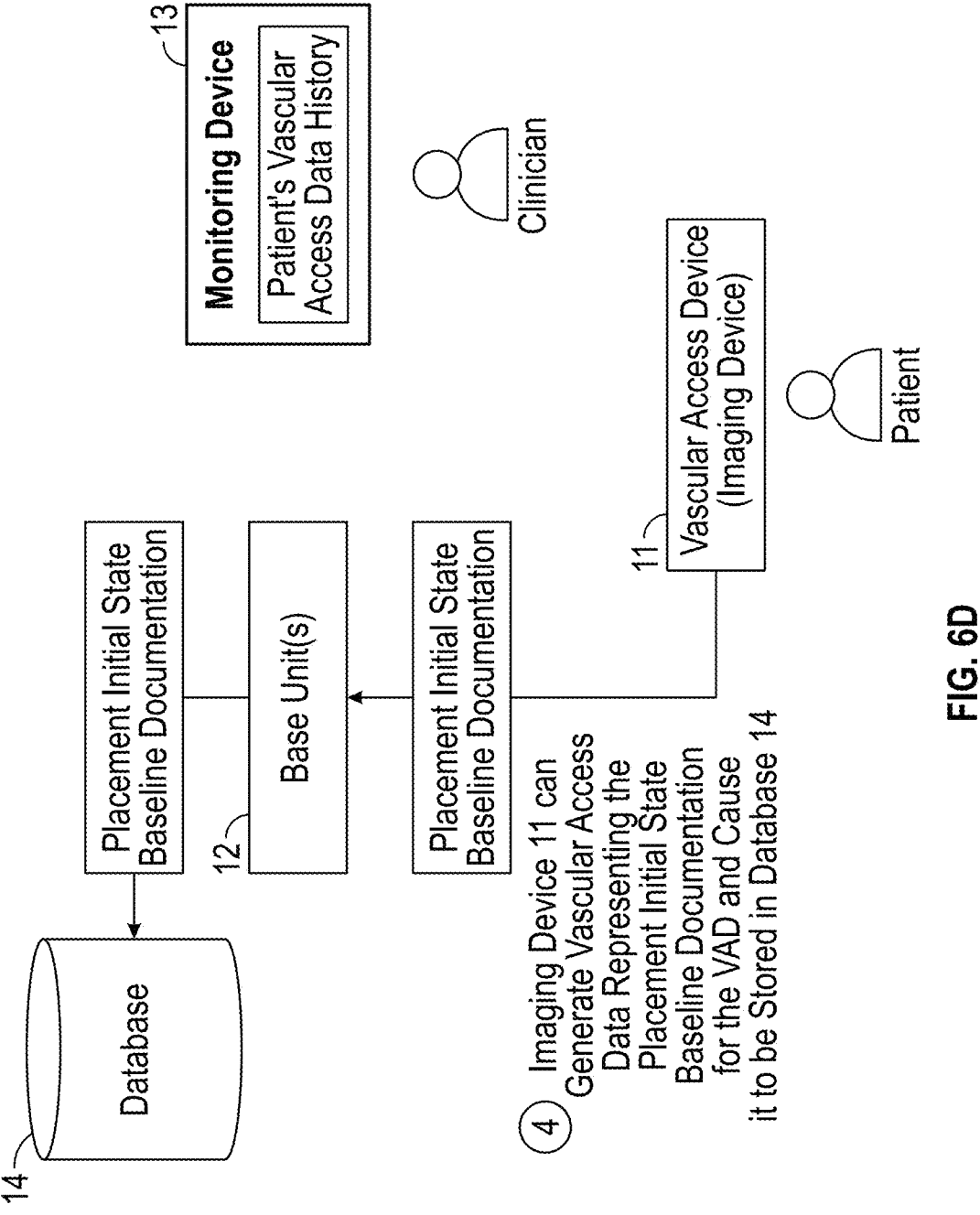
Figure 6E:
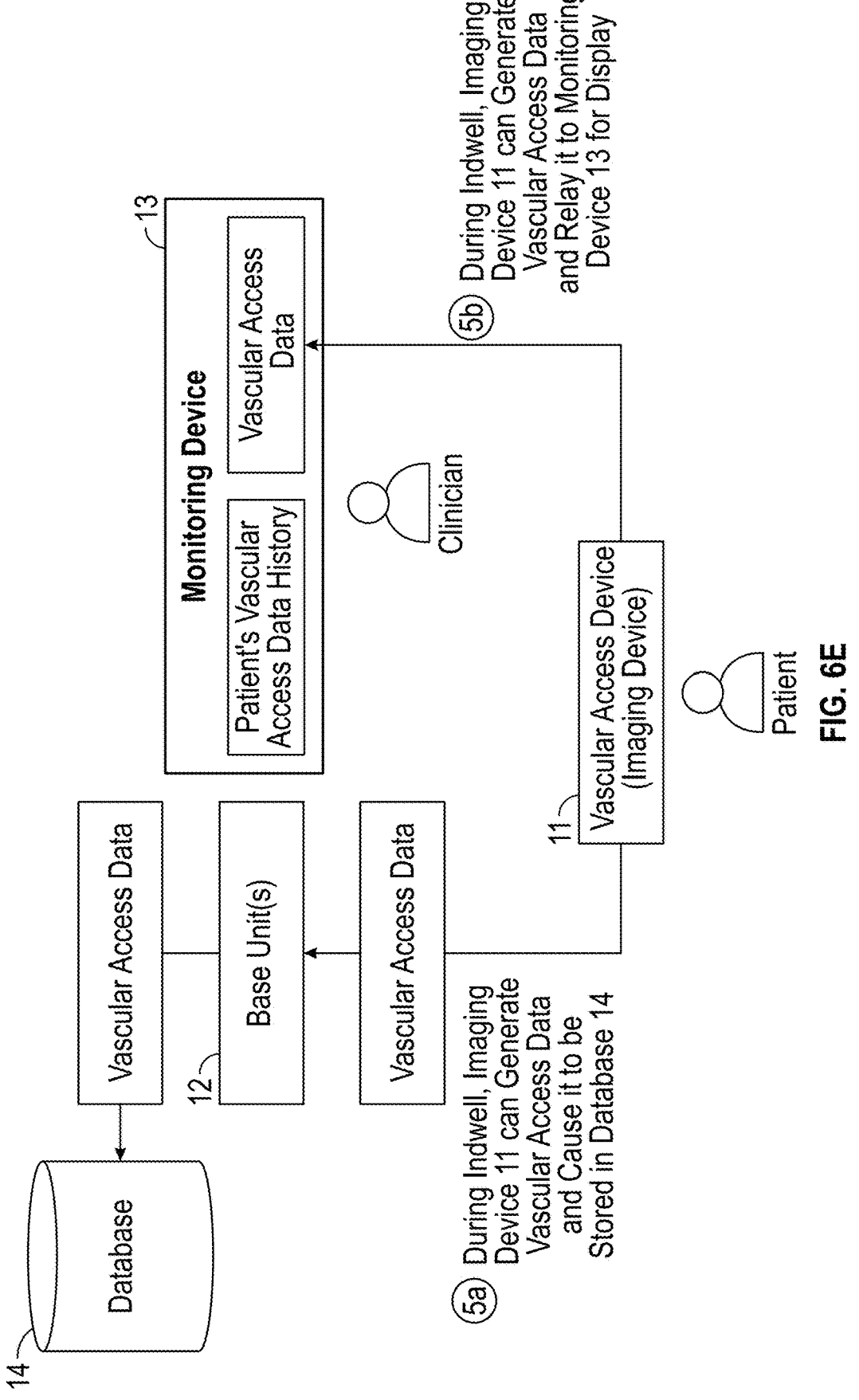
Figure 6F:
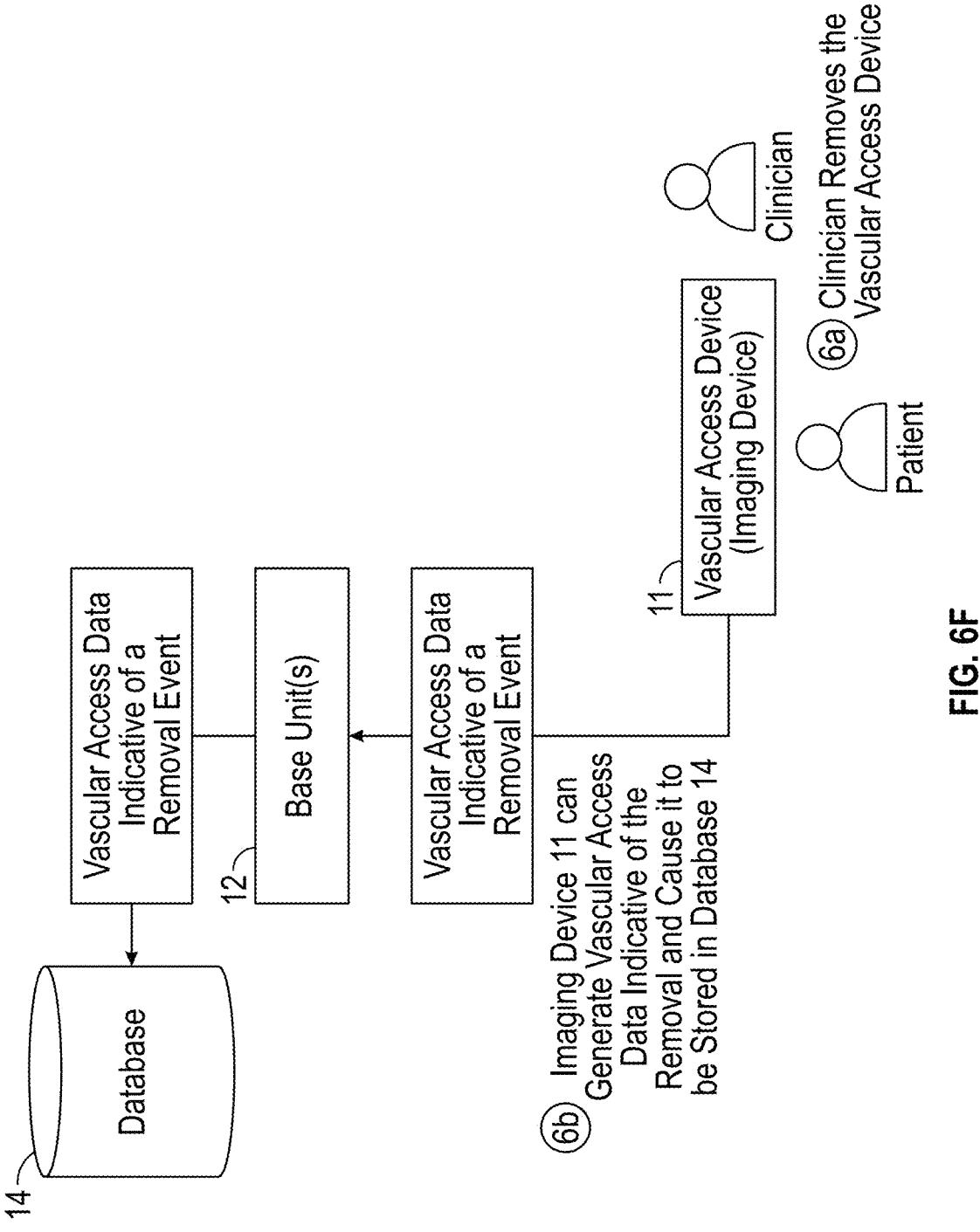
Figure 6G:
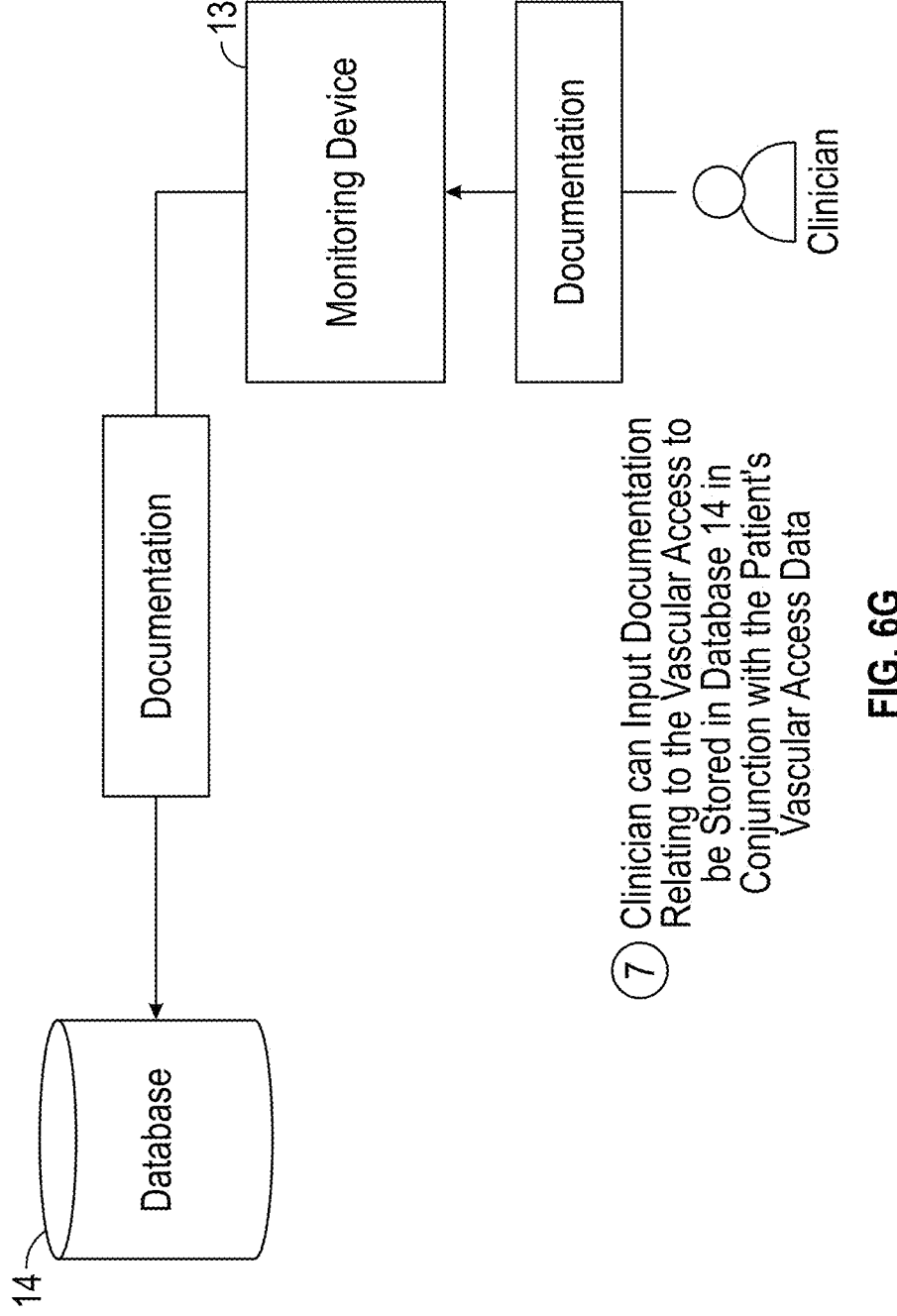
Figure 7:
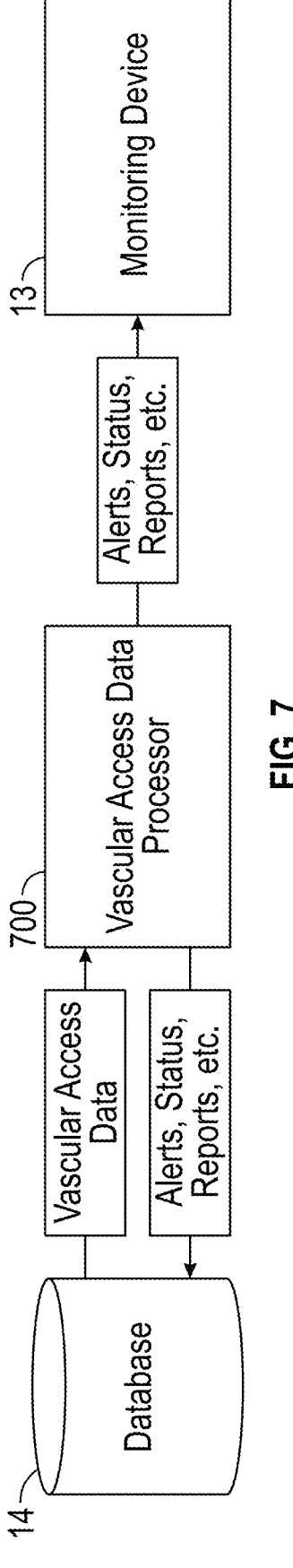

FIG. 3B is a transverse view of a vein in which a catheter is inserted that can be generated by a vascular access device that is configured in accordance with one or more embodiments;

FIG. 3C is a cross-sectional view of a vein in which a catheter is inserted that can be generated by a vascular access device that is configured in accordance with one or more embodiments;

FIG. 4 is an example display that can be generated by a vascular access system that is configured in accordance with one or more embodiments;

FIG. 5 provides an example of electronic components that a base unit or monitoring device of a vascular access system may include in one or more embodiments;

FIGS. 6A-6G provide an example of how vascular access data can be collected and connected throughout the continuity of care; and FIG. 7 provides an example of how vascular access data may be processed.

DESCRIPTION OF EMBODIMENTS

In this specification and the claims, the term "continuity of care" is intended to represent the entire duration of a vascular access including pre-insertion, during insertion, indwell duration, and post-removal. A "vascular access device" should be construed as encompassing an intravenous catheter device and any other device by which a patient's vasculature may be accessed. "Vascular access data" should be construed as encompassing any data relating to the access of a patient's vasculature using a vascular access device and includes images of the patient's vasculature, characteristics of the vascular access device, information about the placement and/or removal of the vascular access device, information about events that occur during the indwell of the vascular access device, complications detected, the patient's vitals, fluid and blood flow characteristics, etc.

Figure 1A:
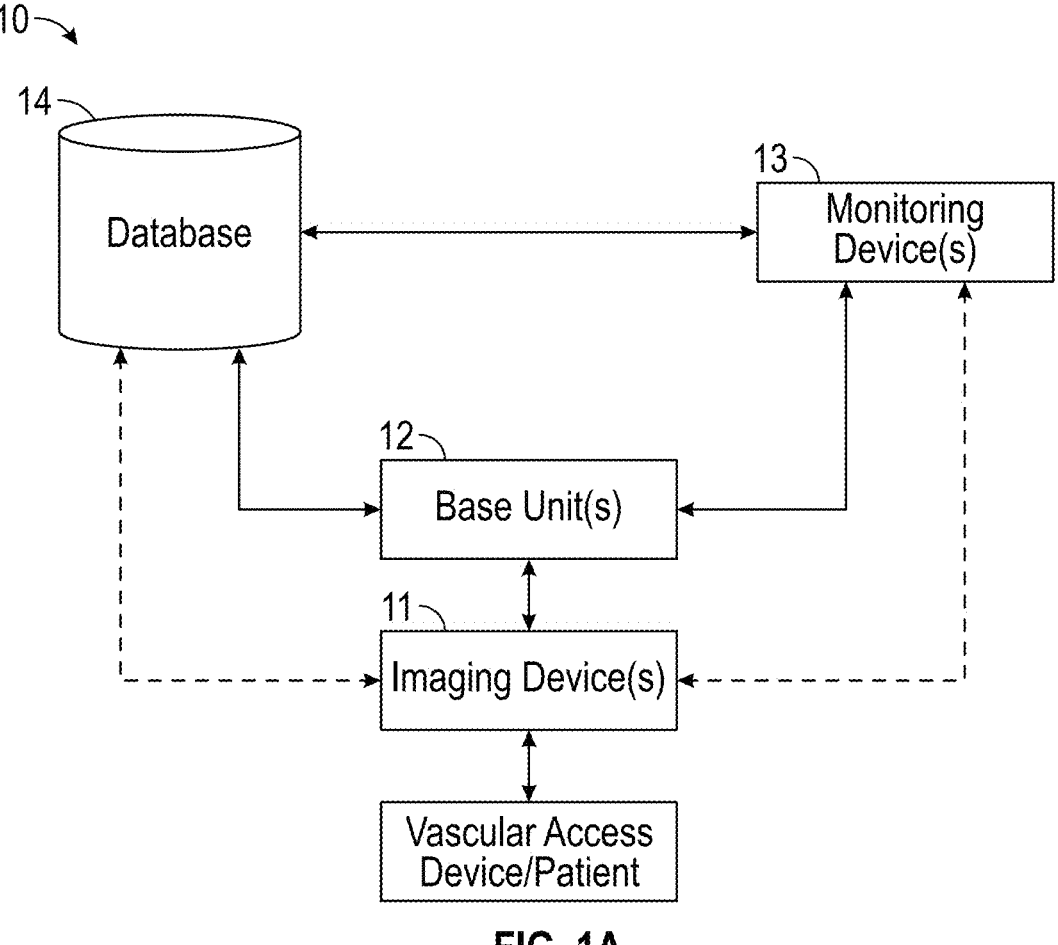
FIG. 1A illustrates an example computing environment in which embodiments may be implemented.

FIG. 1A provides an example of a computing environment 10 in which one or more embodiments may be implemented. Computing environment 10 includes one or more imaging devices 11, one or more base units 12, one or more monitoring devices 13 and a database. Each imaging device 11 can be used to capture images (e.g., via ultrasound or other modality) and possibly other vascular access data in connection with a vascular access device being placed in the vascular of a patient. Examples of imaging devices 11 include separate imaging devices used for performing ultrasound guided intravenous access and ultrasound assemblies that are integrated into the vascular access device such as ultrasound assembly 200 described below with reference to FIGS. 2A-5. In some embodiments, computing environment 10 could include one or more doppler devices that may be used to capture flow characteristics. A doppler device could be used in place of or in addition to an imaging device to provide functionality as described below.

A base unit 12, which may be integrated into another component of computing environment 10 in some embodiments, can represent a networking-capable computing device that is configured to communicate with database 14 and possibly with monitoring device(s) 13. For example, in some embodiments, imaging device 11 may interface directly with base unit 12 (e.g., via Bluetooth or another short-range communication protocol) for communicating vascular access data which in turn may communicate with database 14 for storing such vascular access data and/or with monitoring device(s) 13 for displaying such vascular access data. In other embodiments, imaging device 11 may have such networking capabilities and may therefore be viewed as including base unit 12.

A monitoring device 13 can be any computing device that is configured to display data related to the continuity of care. For example, a monitoring device 13 could be a personal computer, smart phone, dedicated computing device/display, etc. on which a web-based interface or dedicated application is used to display vascular access data pertaining to the continuity of care for a patient. Such monitoring devices 13 could be positioned in the patient's room or at a nursing station, carried by a clinician, etc. In some embodiments, a monitoring device 13 may include a base unit 12. For example, a monitoring device 13 could be placed next to a patient and could implement the functionality of a base unit 12 to interface with an imaging device 11 and database 14.

Database 14 is intended to represent any arrangement of computing components that may be used to store vascular access data for one or more patients. For example, database 14 could be a dedicated server computing device or cloud storage that is configured to implement database functionality.

Figure 1B:
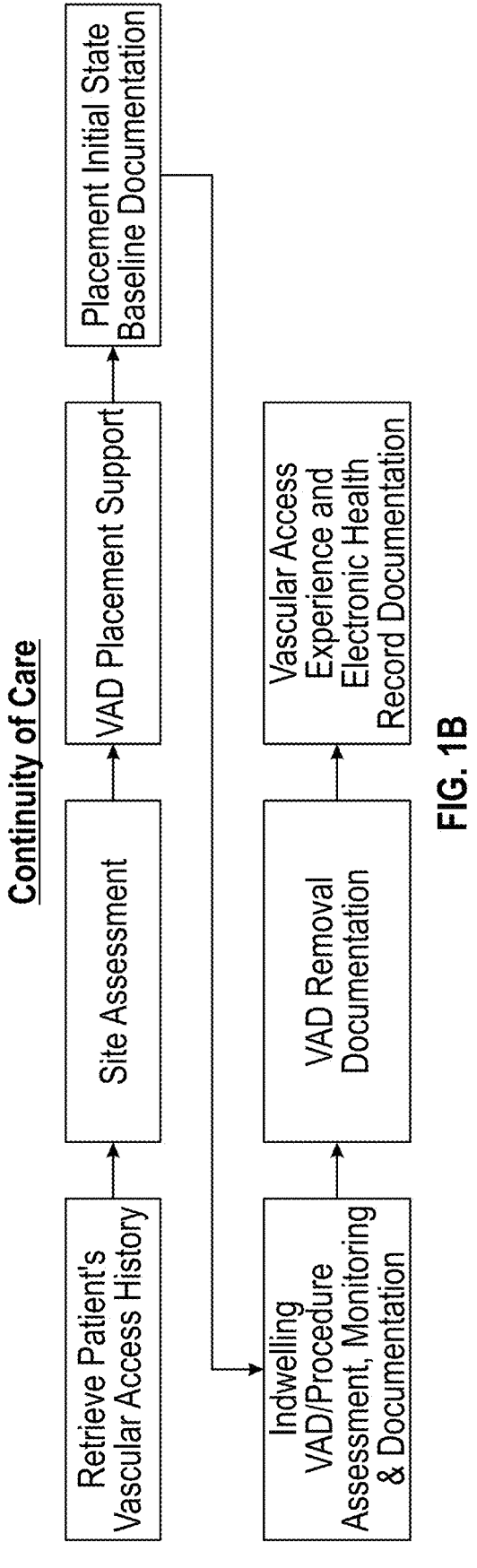
FIG. 1B is a flow diagram represented the continuity of care associated with a vascular access.

FIG. 1B is a flow diagram representing the continuity of care throughout which embodiments enable the capture and connecting of vascular access data. The continuity of care can encompass connecting a patient's vascular access history. In other words, vascular access data pertaining to previous vascular accesses can be retrieved to connect such data throughout the continuity of care of a subsequent vascular access. The continuity of care can also include collecting and/or connecting vascular access data during a site assessment and vascular access device (or VAD) placement support. These stages may entail using one or more imaging devices 11 to examine the location of the patient's veins both prior to and during the placement of a vascular access device such as to identify and select the best vein for placement and to determine the appropriate catheter gauge size and length for the target vein. The one or more imaging devices 11 can be used to generate and/or present vascular access data during these two stages of the continuity of care. The continuity of care can further include collecting vascular access data in the form of placement initial state baseline documentation. This documentation may include a position of the vascular access device within the patient's vasculature, the extent to which the vascular access device is inserted into the patient's vasculature, etc. The continuity of care may also include collecting vascular access data throughout the indwell of the vascular access device such as documentation representing an assessment or monitoring of the patient and/or the vascular access device including during procedures, events, or other occurrences. The continuity of care may additionally include collecting vascular access data constituting documentation of the removal of the vascular access device. Finally, the continuity of care may include collecting vascular access data in the form of vascular access experience and electronic health record documentation (e.g., feedback from the patient and/or one or more clinician's that were involved in the vascular access).

Prior to describing in detail how computing environment 10 may be leveraged to collect and connect vascular access data throughout the continuity of care, some examples of dedicated imaging devices 11 that may be used for this purpose are described. FIGS. 2A-5 address such examples.

Figure 2A:
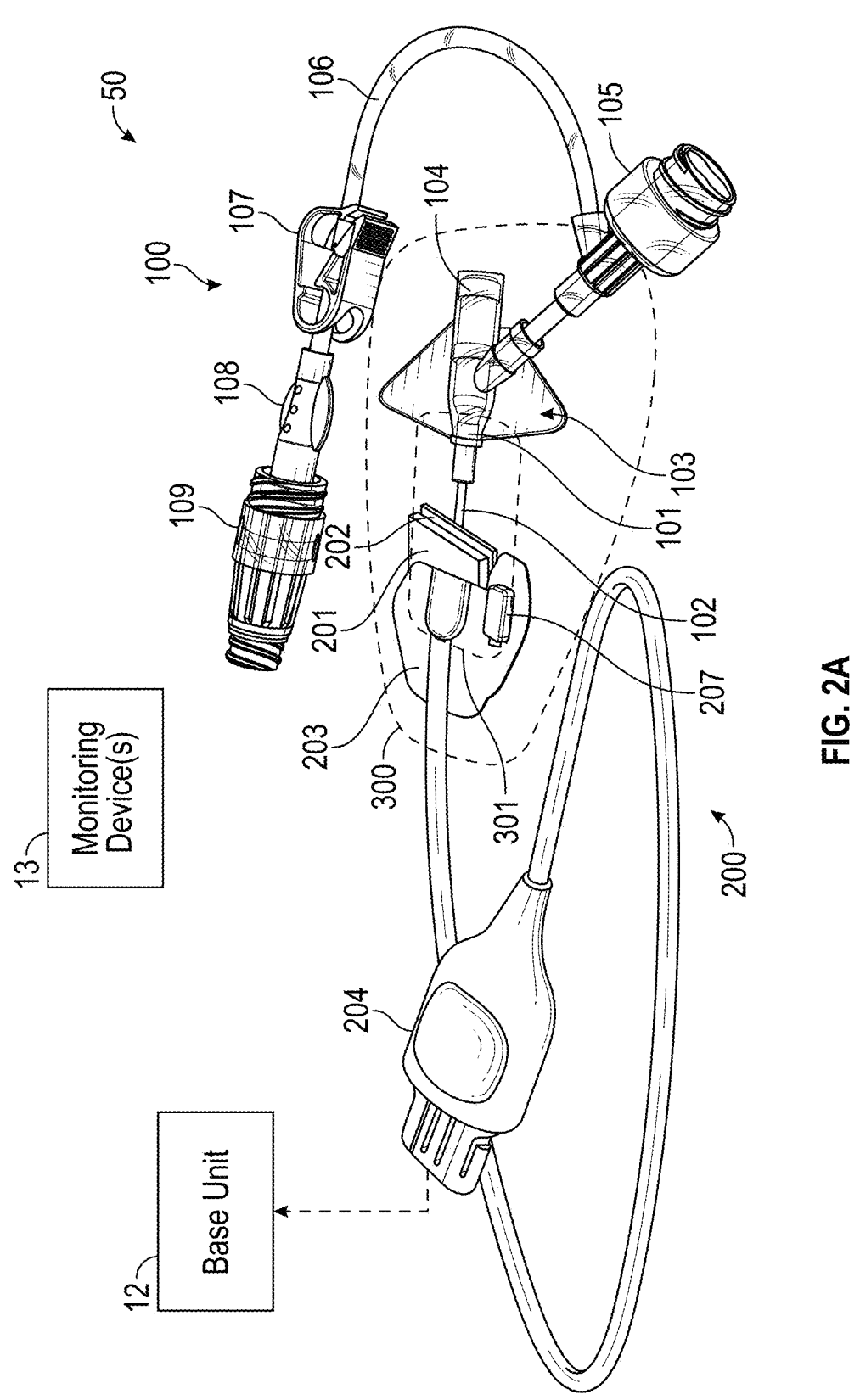
FIG. 2A provides an example of a vascular access system that is configured in accordance with one or more embodiments.

Referring now to FIG. 2A, a vascular access system 50 may include a vascular access device 100, an ultrasound assembly 200 (which is an example of an imaging device 11 that includes a base unit 12), a securement dressing 300, and one or more monitoring devices 13. Vascular access device 100 may include a catheter adapter 101, a catheter 102 that extends distally from catheter adapter 101, a securement platform 103 (e.g., wings that extend outwardly from catheter adapter 101), a needle access port 104 by which an introducer needle (not shown) can be inserted through catheter adapter 101 and catheter 102, a near patient access port 105 which may be connected to a side port of catheter adapter 101, extension tubing 106 having a clamp 107 and to which luer adapter 108 is connected, and an access port 109 coupled to the luer adapter 108. This is only one example of various different configurations of vascular access devices that may be used in vascular access systems that are configured in accordance with embodiments of the present disclosure.

Ultrasound assembly 200 may include an ultrasound probe (or patch) 201 (which is an example of an imaging device 11), a securing mechanism 202 for securing ultrasound probe 201 to the skin and/or to catheter 102, an electrical adapter 203 by which a cable 204 is connected to ultrasound probe 201, and a base unit 12 to which cable 204 may be connected to enable base unit 12 and ultrasound probe 201 to communicate. In some embodiments, securing mechanism 202 may be an adhesive film on the underside of ultrasound probe 201 that may be used to adhere ultrasound probe 201 directly to a patient's skin overtop catheter 102. In some embodiments, securing mechanism 202 can be a mechanical connection between ultrasound probe 201 and catheter adapter 101 and/or catheter 102. In some embodiments, electrical adapter 203 may be separable from ultrasound probe 201, while in other embodiments, electrical adapter 203 may be integrated with ultrasound probe 201. As suggested above, base unit 12 can be any device that includes circuitry for communicating with ultrasound probe 201. In some embodiments, base unit 12 may provide power to ultrasound probe 201. In some embodiments, base unit 12 may directly process images received from ultrasound probe 201, while in other embodiments, base unit 12 may receive images from ultrasound probe 201 and forward the images to another device (e.g., monitoring device(s) 13) for processing. In some embodiments, base unit 12 may include user input elements to allow a user (e.g., a clinician and/or the patient) to control ultrasound probe 201. In some embodiments, base unit 12 may be connected to one or more other devices to allow users of the one or more other devices (e.g., monitoring device(s) 13) to control ultrasound probe 201.

Securement dressing 300 may be sized and shaped to cover and secure ultrasound probe 201 and catheter adapter 101 against the patient's skin. For example, in some embodiments, securement dressing 300 may fully cover catheter adapter 101 and may include an opening through which extension tubing 106 extends. The underside of securement dressing 300 may be adhesive to prevent securement dressing 300 from moving once placed on the skin. In some embodiments, a transparent window 301 may be formed in securement dressing 300 to facilitate viewing catheter 102 and ultrasound probe 201.

In some embodiments, ultrasound probe 201 may be integrated into securement dressing 300. In other embodiments, ultrasound probe 201 may be separate from securement dressing 300. In such embodiments, ultrasound probe 201 may be placed overtop catheter 102 and then securement dressing 300 may be placed overtop ultrasound probe 201 and catheter adapter 101. In any case, ultrasound probe 201 can be positioned on the patient's skin so that it is overtop the distal tip of catheter 102 when catheter 102 is inserted into the patient's vasculature.

As suggested above, monitoring device(s) 13 can represent any device having a display on which images generated by ultrasound probe 201 may be displayed and/or on which information obtained from such images may be displayed. As examples, monitoring device(s) 13 could include a smart phone, a tablet, a laptop, a desktop, a thin client, a television, a dedicated display device, an infusion pump, a patient vital sign monitor, an arterial monitor, an ultrasound system visual display, etc. In some embodiments, a monitoring device 13 could function as base unit 12. A monitoring device 13 could also be configured to interface with one or more separate computing systems such as a system for storing vascular access data in database 14.

Figure 2B:
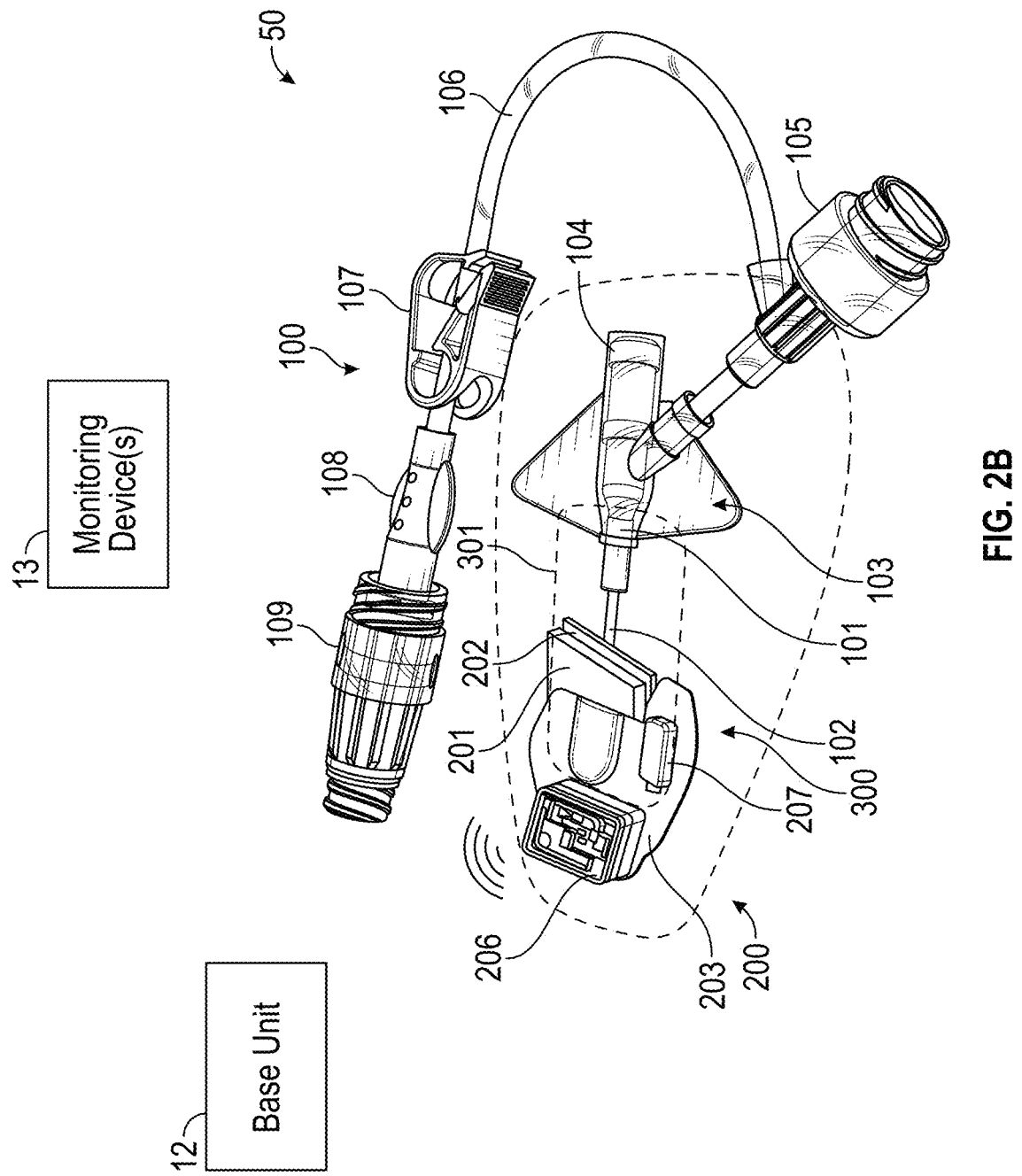
FIG. 2B provides another example of a vascular access system that is configured in accordance with one or more embodiments.

FIG. 2B provides another example configuration of vascular access system 50 in which a wireless adapter 206 in used in place of cable 204. Wireless adapter 206 may be configured to transmit images generated by ultrasound probe 201 to base unit 12 or possibly to monitoring device(s) 13. Wireless adapter 206 may also include batteries for powering ultrasound probe 201. In some embodiments, wireless adapter 206 may be integrated into electrical adapter 203, while in other embodiments, wireless adapter 206 may be selectively coupled to electrical adapter 203.

FIGS. 2A and 2B provide examples where vascular access system 50 includes a peripheral intravenous catheter. However, a vascular access system configured in accordance with embodiments of the present disclosure could be used with central venous catheters, peripherally inserted central catheters, midline catheters, arterial catheters, ports, venipuncture, sub-cutaneous access devices, or other indwelling tube, probe, sensor, or instrument.

FIG. 3A is a partial cross-sectional view of vascular access system 50 when used on a patient. As shown, ultrasound probe 201 may be positioned via securing mechanism 202 on the patient's skin overtop a distal tip 102a of catheter 102 when catheter 102 is inserted into the patient's vasculature 501. Securement dressing 300 can be positioned overtop catheter adapter 101 and ultrasound probe 201 to retain this positioning of ultrasound probe 201 overtop distal tip 102a. In this position, ultrasound probe 201 can generate ultrasound images continuously, periodically, on demand, by events triggering an image to be captured, etc. of the portion of vasculature 501 within which catheter 102 extends including the surrounding tissue. For example, FIG. 3B is an image that captures a transverse view of vasculature 501, catheter 102, and distal tip 102a, and FIG. 3C is an image that captures a cross-sectional view of vasculature 501 and catheter 102.

FIG. 4 provides an example of how images generated by ultrasound probe 201 can be integrated into a display along with various information derived from the images. As indicated, this display could be generated and/or presented on base unit 12 and/or any number of monitoring devices 13. This display may include one or more views of catheter 102 within vasculature 501 such as the transverse view of FIG. 3B and the cross-sectional view of FIG. 3C. The transverse view may allow a clinician to see how catheter 102 is extending into vasculature 501 and may therefore facilitate quickly determining if catheter 102 is inserted sufficiently, if distal tip 102a is positioned correctly, if there is any blockage, or any other condition that is capable of being detected via ultrasound. The cross-sectional view may allow a clinician to see how a particular portion of catheter 102 is positioned within vasculature 501 and may therefore facilitate quickly determining if catheter 102 may be excessively limiting blood flow through vasculature 501 or any other condition that is capable of being detected via ultrasound. In some embodiments, a user may be able to adjust the location of the views generated by ultrasound probe 201. For example, a user may be able to move the cross-sectional view along the length of catheter 102 to determine if there is excessive blockage at any portion along the length of catheter 102.

FIG. 4 also illustrates that the display may include a variety of vascular access data that may be derived from the images that ultrasound probe 201 produces or from input. For example, the display includes an indicator 601a of the gauge of catheter 102 and an indicator 601b of the length of catheter 102. Indicators 601a and 601b could be obtained via user input or could be calculated from the images produced by ultrasound probe 201.

The display also includes indicators 602a, 602b, and 602c for different parameters. In some embodiments, these parameters could be selectable. For example, in FIG. 4, indicator 602a provides information for when catheter 102 was last flushed. This last flush information could be calculated using the images produced by ultrasound probe 201. For example, doppler techniques could be applied to the image data to detect when fluid is flowing out through distal tip 102a, and in response to such a detection, base unit 12 (or a monitoring device 13) could automatically store an indication that a flush has occurred at that time. In FIG. 4, indicators 602b and 602c have not been selected. However, these indicators and additional indicators could be selected to display information for any of many different conditions, events, statuses, etc. as described below.

The display further includes indicators 603a and 603b that provide information about the portion of catheter 102 that is inside vasculature 501. Indicator 603a defines the catheter to vein ratio (i.e., the ratio of the catheter's diameter to the vein's diameter at a particular location). Indicator 603b defines the purchase of catheter 102 (i.e., the length of catheter 102 that is inside vasculature 501 or the percentage of the catheter length that is inside the vasculature). The display additionally includes an indicator 604 defining a patency status of catheter 102 (i.e., whether catheter 102 can safely remain within vasculature 501). Base unit 12 (or a monitoring device 13) could calculate the patency status using the images provided by ultrasound probe 201 (e.g., to detect the extent to which catheter 102 and/or vasculature 501 around catheter 102 may be blocked).

As suggested above, vascular access system 50 can be configured to monitor and/or display information relating to the status of catheter 102, vasculature 501, or the surrounding tissue and a variety of associated physiological or procedural parameters by leveraging images that are provided by ultrasound probe 201. This information includes catheter geometry information (e.g., the catheter to vein ratio, the purchase of the catheter, flow restrictions around the catheter), catheter position information (axial position of the catheter within the vein, the position or angle of the distal tip of the catheter relative a vein wall, valve, branch or other physiological feature), catheter movement or displacement, catheter kinking, dislodgment events, extravasation, infiltration detection (e.g., by monitoring tissue surrounding vasculature 501), thrombus development, phlebitis (visual or correlated cumulative movement), patency indicators, blood flow characteristics (e.g., by using doppler to detect velocity and/or volume of blood flowing into catheter 102), fluid administration flow characteristics (e.g., by using doppler to detect velocity, volume, direction, and/or duration of fluid flow), procedural events (e.g., flush, draw, fluid administration), and/or line draw tubing, probe or sensor position in the vein or relative to the distal tip of the catheter or physiological feature (e.g., thrombus, valve, wall, branch, etc.).

Vascular access system 50 may provide a display including indicators of any of the above-mentioned information and may provide corresponding alerts. For example, base unit 12 or a monitoring device 13 may be configured to output a visual, audible, tactile, or digital alert when a condition or event is detected from the ultrasound images. In some embodiments, ultrasound probe 201, electrical adapter 203, cable 204, and/or wireless adapter 206 could include one or more alerting mechanisms (e.g., LEDs, speakers, haptic units, etc.) to provide an alert.

FIG. 5 provides an example of how base unit 12 (or possibly monitoring device 13) could be configured to generate display content from ultrasound images. This display content can include any of the above-described information, indicators, status, events, alerts, etc. (collectively "parameters"). FIG. 4 is one example of display content.

Base unit 12 may be configured to receive ultrasound images from ultrasound probe 201 continuously, periodically, on demand, etc. Base unit 12 may include an image processor 12a that is configured to process the ultrasound images to generate processing image data. This processed image data can be input to an artificial intelligence engine 12b that may be configured to detect and/or generate parameters from the processed image data. The parameters along with the ultrasound images can be provided to a display module 12c that can generate the display content that includes the images and the parameters.

In some embodiments, image processor 12a can be configured to determine from an image or sequence of images various status information such as catheter geometry or position information or the presence of a thrombus, kink, or other blockage. In some embodiments, artificial intelligence engine 12b can be trained to detect when parameters are present in a stream of ultrasound images. For example, artificial intelligence engine 12b could detect when a sequence of ultrasound images is indicative of a flush event, a draw event, the occurrence of extravasation, a dislodgement or movement event, etc. In some embodiments, artificial intelligence engine 12b could be used to predict the development or increasing risk of a potential complication or event. For example, artificial intelligence engine 12b could process ultrasound images to detect that the catheter purchase is changing or decreasing over time. If this trend is detected or a threshold purchase is reached (e.g., when less than some percentage of catheter length remains in the vein), artificial intelligence engine 12b could cause an alert to be triggered so that a clinician can prevent failure of the catheter.

FIGS. 6A-6G provide an example of how vascular access data can be collected and connected throughout the continuity of care. Turning to FIG. 6A, it is assumed that a clinician intends to insert a vascular access device into a patient's vasculature. As part of the pre-insertion planning, the clinician may use a monitoring device 13 to request vascular access data history for the patient. In step 1b, monitoring device 13 can interface with database 14 to retrieve the vascular access data history for the patient. For example, monitoring device 13 could use a patient identifier to query database 14 for any vascular access data associated with the patient.

Turning to FIG. 6B, in step 2, the clinician can review the patient's vascular access data history on monitoring device 13. For example, the patient's vascular access data history could include vascular access data collected during previous vascular accesses and may identify placement time, placement location (e.g., which body part, which vein, etc.), removal time, events, difficulties, images, etc., such as are described in further detail below. By reviewing this vascular access data history, the clinician may be better informed and better able to successfully place the vascular access device (e.g., by avoiding a placement location where a previous access attempt failed and/or where many difficulties occurred).

Turning to FIG. 6C, in step 3a and after/while considering the patient's vascular access data history, the clinician may use an imaging device 11 to perform a site assessment and/or for placement support during placement of the vascular access device. For example, the clinician could use monitoring device 13 to view an image of or information about a previous placement that is included in the patient's vascular access data history and may consider the image or information while using an imaging device 11 to identify a suitable location to insert the vascular access device. In some embodiments, in step 3b, imaging device 11 can generate and send to database 14 vascular access data pertaining to the site assessment and/or the vascular access device placement support.

Turning to FIG. 6D, it is now assumed that the clinician has placed the vascular access device in the patient's vasculature. In step 4, imaging device 11 can generate vascular access data representing the placement initial state baseline documentation and cause it to be stored in database 14 (e.g., via base unit 12). In the depicted embodiment, it is assumed that an imaging device 11 similar to ultrasound assembly 200 is used as part of the vascular access and will therefore be capable of continuously generating vascular access data throughout the indwell of the vascular access device.

The placement initial state baseline documentation can identify geometric and/or position information about the vascular access device within the patient's vasculature. For example, this documentation could define the catheter to vein ratio, the purchase of the catheter, the axial position of the catheter, a tip position or angle of the catheter relative to a wall, valve, branch, etc. of the vasculature, any flow restrictions, etc. In short, this baseline documentation can identify where the catheter is initially positioned in the vasculature.

Turning to FIG. 6E, in step 5a, imaging device 11 can generate vascular access data throughout the indwell of the vascular access device and cause the data to be stored in database 14. Similarly, in step 5b, imaging device 11 may cause such data to be displayed on monitoring device 13. In cases where imaging device 11 may be integrated into the vascular access device similar to ultrasound assembly 200, steps 5a and/or 5b could be continuously and automatically performed. However, if imaging device 11 is a separate component, a clinician could use the imaging device periodically to generate vascular access data.

A wide variety of vascular access data can be collected during the indwell of the vascular access device. For example, this vascular access data could represent (e.g., as images and/or data) catheter movement or displacement, catheter kinking, dislodgement events, extravasation, infiltration, thrombus development, phlebitis (e.g., visual or correlated cumulative movement), patency indicators, blood flow characteristics in the vein or during aspiration or blood collection (e.g., velocity, volume, direction, via doppler, etc.), fluid administration flow characteristics (e.g., velocity, volume, direction, duration, etc.), procedural events (e.g., flush, draw, fluid administration, etc.), line draw tubing, probe or sensor position in the vein or relative to the catheter tip or physiological feature (e.g., thrombus, valve, wall, branch, etc.), etc. In some embodiments, the procedural events could be automatically detected (e.g., using artificial intelligence and/or image processing such as is represented in FIG. 7 below) or manually detected (e.g., via clinician input to imaging device 11 and/or monitoring device 13).

Turning to FIG. 6F, in step 6a, it is assumed that the clinician removes the vascular access device from the patient's vasculature. In step 6b, imaging device 11 can automatically generate vascular access data indicative of the removal (e.g., removal time, reason for removal, etc.) and cause it to be stored in database 14. Alternatively, in some embodiments, the clinician may use imaging device 11 and/or monitoring device 13 to manually generate vascular access data indicative of the removal.

Turning to FIG. 6G, in step 7, the clinician may input (e.g., to monitoring device 13) additional vascular access data in the form of documentation of the vascular access experience or other documentation relevant to the patient's electronic health record. At this point, database 14 can maintain vascular access data pertaining to the continuity of care of the vascular access which data can become part of the patient's vascular access data history.

In summary, the process in FIGS. 6A-6G represents that historic vascular access data can be retrieved and presented to the clinician throughout the continuity of care and that current vascular access data can be generated and collected throughout the continuity of care. Embodiments enable all this vascular access data to be considered together at any point during the continuity of care.

In some embodiments, the vascular access data stored in database 14 can be processed to generate alerts, status, reports, etc. Such processing could be performed during the vascular access (e.g., in real-time) or after (e.g., to perform a diagnosis, as part of research, etc.). FIG. 7 provides an example where a vascular access data processor 700 can interface with database 14 to retrieve and process vascular access data to produce alerts, status, reports, etc. which can be presented via monitoring device 13 and/or stored in database 14. Vascular access data processor 700 may use various algorithms, artificial intelligence, or other processing techniques for this purpose. In some embodiments, vascular access data processor 700 could be a standalone computing device, while in other embodiments, vascular access data processor 700 could be integrated into an imaging device 11 or monitoring device 13.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed:
1. A method for collecting and connecting vascular access data comprising:
  storing in a database historic vascular access data representing a history of a patient's vascular access, the historic vascular access data including ultrasound images of a portion of the patient's vasculature;
  presenting via a monitoring device the historic vascular access data during an access of the patient's vasculature;

detecting, by a base unit of an ultrasound assembly, that an ultrasound probe of the ultrasound assembly has been adhered to the patient's skin overtop the portion of the patient's vasculature into which a catheter has been or will be inserted to perform the access of the patient's vasculature;
  collecting, by the base unit, additional vascular access data during the access of the patient's vasculature, by receiving, from the ultrasound probe, additional ultrasound images which capture the portion of the patient's vasculature into which the catheter is inserted; and
  storing in the database the additional vascular access data with the historic vascular access data.
2. The method of claim 1, wherein the historic vascular access data comprises one or more images of the patient's vasculature.
3. The method of claim 1, wherein the additional ultrasound images comprise one or both of transverse views and cross-sectional views of the portion of the patient's vasculature.
4. The method of claim 1, wherein presenting via the monitoring device the historic vascular access data during the access of the patient's vasculature comprises presenting via the monitoring device the historic vascular access data during a site assessment before inserting the catheter into the portion of the patient's vasculature or while performing placement support during insertion of the catheter into the portion of the patient's vasculature.
5. The method of claim 4, wherein collecting, by the base unit, the additional vascular access data during the access of the patient's vasculature also comprises receiving, from the ultrasound probe, further ultrasound images which capture the portion of the patient's vasculature during the site assessment or while performing the placement support.
6. The method of claim 1, wherein the additional ultrasound images which capture the portion of the patient's vasculature into which the catheter is inserted comprise placement initial state baseline documentation.
7. The method of claim 6, wherein the placement initial state baseline documentation identifies one or both of geometric and position information of the catheter within the portion of the patient's vasculature.
8. The method of claim 7, further comprising:
  processing the additional ultrasound images to generate one or more alerts, status, or reports.
9. The method of claim 8, wherein the one or more alerts, status, or reports are generated while the catheter remains inserted into the portion of the patient's vasculature.
10. The method of claim 1, further comprising:
  processing the additional ultrasound images to identify a removal of the catheter from the portion of the patient's vasculature.
11. A method for connecting and collecting vascular access data throughout continuity of care comprising:
  storing in a database historic vascular access data representing a history of a patient's vascular access;
  presenting via a monitoring device the historic vascular access data during an access of the patient's vasculature;
  detecting, by a base unit of an ultrasound assembly, that an ultrasound probe of the ultrasound assembly has been adhered to the patient's skin overtop a portion of the patient's vasculature into which a catheter will be inserted to perform the access of the patient's vasculature;
  collecting, by the base unit, first vascular access data during a site assessment or placement support of the access of the patient's vasculature, the first vascular access data comprising first ultrasound images of the portion of the patient's vasculature which are generated by the ultrasound probe before the catheter is inserted into the portion of the patient's vasculature;

collecting, by the base unit, second vascular access data representing a placement initial state baseline documentation for the access of the patient's vasculature, the second vascular access data comprising second ultrasound images of the portion of the patient's vasculature which are generated by the ultrasound probe after the catheter is inserted into the portion of the patient's vasculature; and collecting, by the base unit, third vascular access data during indwell of the catheter, the third vascular access data comprising third ultrasound images of the portion of the patient's vasculature which are generated by the ultrasound probe while the catheter remains inserted into the portion of the patient's vasculature.

12. The method of claim 11, further comprising:

collecting, by the base unit, fourth vascular access data representing a removal of the vascular access device, the fourth vascular access data comprising fourth ultrasound images of the portion of the patient's vasculature which are generated by the ultrasound probe as the catheter is removed from the portion of the patient's vasculature.

13. The method of claim 12, further comprising:

collecting vascular access data representing an experience of the access of the patient's vasculature.

14. The method of claim 11, wherein the third vascular access data represents one or more of: catheter movement or displacement, catheter kinking, dislodgement events, extravasation, infiltration, thrombus development, phlebitis, patency indicators, blood flow characteristics, fluid administration flow characteristics, procedural events, line draw tubing, or probe or sensor position.

15. The method of claim 14, further comprising:

processing the vascular access data to automatically detect the procedural events.

16. A system for collecting and connecting vascular access data throughout continuity of care comprising:

a database storing historic vascular access data representing a history of a patient's vascular access, the historic vascular access data including ultrasound images of a portion of the patient's vasculature;

one or more monitoring devices that are configured to present the historic vascular access data during an access of the patient's vasculature; and an ultrasound assembly configured to generate additional vascular access data during the access of the patient's vasculature and to store the additional vascular access data in the database in association with the historic vascular access data, wherein the ultrasound assembly comprises an ultrasound probe and a securing mechanism for securing the ultrasound probe to the patient's skin throughout the access of the patient's vasculature and to position the ultrasound probe overtop a portion of the patient's vasculature into which a catheter has been or will be inserted to perform the access of the patient's vasculature, and wherein the additional vascular access data comprises ultrasound images capturing a portion of the patient's vasculature into which the catheter is inserted throughout the access of the patient's vasculature.

17. The system of claim 16, further comprising:

one or more doppler devices configured to generate further vascular access data during the access of the patient's vasculature and to store the further vascular access data in the database in association with the historic vascular access data and the additional vascular access data.

18. The system of claim 16, wherein the ultrasound images comprise transverse views of the portion of the patient's vasculature.

19. The system of claim 16, wherein the ultrasound images comprise cross-sectional views of the portion of the patient's vasculature.

20. The system of claim 16, wherein the one or more monitoring devices are configured to present the historic vascular access data during a site assessment or placement support of the access of the patient's vasculature.

* * * * *